US010813594B2

(12) United States Patent
Deng (10) Patent No.: US 10,813,594 B2
(45) Date of Patent: *Oct. 27, 2020

(54) CIRCUITS FOR WEARABLE ECG SYSTEM

(71) Applicant: Chunlian Deng, Shenzhen (HK)

(72) Inventor: Chunlian Deng, Shenzhen (HK)

(73) Assignee: SHENZHEN DANSHA TECHNOLOGY CO., LTD., Shenzhen, Guangdong (CN)

( * ) Notice: Subject to any disclaimer, the term of this patent is extended or adjusted under 35 U.S.C. 154(b) by 163 days.

This patent is subject to a terminal disclaimer.

(21) Appl. No.: 16/026,010

(22) Filed: Jul. 2, 2018

(65) Prior Publication Data

US 2018/0310887 A1 Nov. 1, 2018

Related U.S. Application Data

(63) Continuation-in-part of application No. 15/207,659, filed on Jul. 12, 2016, now Pat. No. 10,058,288.

(51) Int. Cl.
| | |
|---|---|
| *A61B 5/00* | (2006.01) |
| *A61B 5/0428* | (2006.01) |
| *A61B 5/024* | (2006.01) |
| *A61B 5/0245* | (2006.01) |
| *A61B 5/0408* | (2006.01) |

(52) U.S. Cl.
CPC .......... *A61B 5/7225* (2013.01); *A61B 5/0245* (2013.01); *A61B 5/02438* (2013.01); *A61B 5/0408* (2013.01); *A61B 5/0428* (2013.01); *A61B 2562/0219* (2013.01)

(58) Field of Classification Search
CPC . A61B 5/721; A61B 5/04018; A61B 5/04085; A61B 5/04288; A61B 5/7246; A61B 2560/0223; A61B 2562/0219; A61B 5/7225; A61B 5/02438; A61B 5/0245; A61B 5/0408; A61B 5/0428
USPC ......................................................... 600/522
See application file for complete search history.

(56) References Cited

U.S. PATENT DOCUMENTS

| | | | | | |
|---|---|---|---|---|---|
| 4,781,201 | A | * | 11/1988 | Wright ................ | A61B 5/0205 600/484 |
| 2010/0041975 | A1 | * | 2/2010 | Chen .................. | A61B 5/04085 600/393 |
| 2011/0077538 | A1 | * | 3/2011 | Liu ...................... | A61B 5/0452 600/509 |

(Continued)

*Primary Examiner* — Erin M Piateski (57) ABSTRACT

A wearable ECG system includes a plurality of electrodes; a multiplexor, the multiplexor including an input port, two output ports, and a control port, the input port of the multiplexor being connected with the electrodes; an analog detection module being connected with one output port of the multiplexor; a digital detection module being connected with the other output port of the multiplexor; a processor being connected with the control port of the multiplexor and the digital detection module; and a motion detection module connected with the processor and configured to detect acceleration of the wearable ECG system and output an electrical signal accordingly. The processor is configured to receive the electrical signal from the motion detection module, and control the multiplexor to selectively transmit output of the electrodes to the analog detection module or the digital detection module based on the electrical signal.

20 Claims, 5 Drawing Sheets

(56) References Cited

U.S. PATENT DOCUMENTS

| | | | |
|---|---|---|---|
| 2014/0278229 A1* | 9/2014 | Hong | A63B 71/06 |
| | | | 702/160 |
| 2016/0135705 A1* | 5/2016 | Liu | A61B 5/04012 |
| | | | 600/509 |
| 2016/0374618 A1* | 12/2016 | Giovangrandi | A61B 5/024 |
| | | | 600/393 |
| 2017/0238847 A1* | 8/2017 | Inan | A61B 5/02125 |

* cited by examiner

CIRCUITS FOR WEARABLE ECG SYSTEM

CROSS-REFERENCE TO RELATED APPLICATIONS

This application claims the benefit of U.S. non-provisional patent application Ser. No. 15/207,659 filed on Dec. 8, 2016, now U.S. Pat. No. 10,058,288; the contents of which is hereby incorporated by reference.

FIELD OF THE PATENT APPLICATION

The present patent application generally relates to medical electronics and more specifically to a wearable ECG (electrocardiogram) system.

BACKGROUND

An ECG (electrocardiogram) system is a widely applied medical examination and monitoring instrument that produces an electrocardiogram (ECG) waveform. A typical ECG waveform includes a series of characteristic points designated by the letters P, Q, R, S, and T. The Q, R, and S portions of the wave when taken together are referred to as a "QRS complex". The R-wave of the QRS complex is the most prominent portion in each cardiac cycle of an ECG signal. In various ECG applications, it is crucial for the ECG system to accurately determine the timing of R-wave peaks.

A conventional ECG system includes an analog frontend circuit, an ADC and a digital signal processor to carry out the task of determining R-wave peaks. Typically, the ADC and the digital signal processor consume a great amount of power, which is often many times of the power consumed by the analog frontend circuit. Relatively large power consumption and considerable complexity of the circuit makes such an ECG system not suitable to be worn by a user so as to constantly examine and monitor heart conditions of the user.

On the other hand, to reduce system power consumption, the ADC and the digital signal processor are eliminated in some wearable ECG systems, so that the determination of ECG are solely relied on pure analog circuits. However, when there are a lot of noises present in the signal acquired by the ECG system, for example, when the person being tested is in motion, it is difficult for pure analog circuits to accurately determine ECG, which therefore greatly limits the application scenarios of such wearable ECG systems.

SUMMARY

The present patent application is directed to a wearable ECG system. In one aspect, the wearable ECG system includes: a plurality of electrodes; a multiplexor, the multiplexor including an input port, two output ports, and a control port, the input port of the multiplexor being connected with the electrodes; an analog detection module being connected with one output port of the multiplexor; a digital detection module being connected with the other output port of the multiplexor; a processor being connected with the control port of the multiplexor and the digital detection module; and a motion detection module, connected with the processor and configured to detect acceleration of the wearable ECG system and output an electrical signal accordingly. The processor is configured to receive the electrical signal from the motion detection module, and control the multiplexor to selectively transmit output of the electrodes to the analog detection module or the digital detection module based on the electrical signal. The digital detection module includes a fourth amplifier; a fifth amplifier being connected with the fourth amplifier; an ADC being connected with the fifth amplifier; and a digital signal processing circuit being connected with the ADC. The digital signal processing circuit and the ADC are respectively connected with the processor. The fourth amplifier has a gain of 30 dB-36 dB, while the fifth amplifier has a gain of 18 dB-25 dB. The digital signal processing circuit includes a first filter; a second filter; a third filter, the second and the third filters being respectively connected with the first filter; a waveform buffer being connected with the first, second and third filters respectively; and a maximum value searcher being connected with the second and the third filters and the processor respectively.

The second and the third filters may be configured to execute computation in an alternating fashion, the computing time of which are overlapped by a predetermined period. The first filter may be a QSWT (Quadratic Spline Wavelet) filter configured to filter baseline shift of the wearable ECG system and human caused noise. The second and the third filters may be respectively configured to execute STAC (Short-term Autocorrelation) algorithm so as to filter myoelectric noise and noise caused by motion of the electrodes. The QSWT filter may include multiple adders and multiple shift operators, while the second and the third filters may respectively include a correlation coefficient buffer, the correlation coefficient buffers of the second and the third filters being respectively synchronized with the ADC.

In another aspect, the present patent application provides a wearable ECG system that includes: a plurality of electrodes; a multiplexor, the multiplexor including an input port, two output ports, and a control port, the input port of the multiplexor being connected with the electrodes; an analog detection module being connected with one output port of the multiplexor; a digital detection module being connected with the other output port of the multiplexor; a processor being connected with the control port of the multiplexor and the digital detection module; and a motion detection module, connected with the processor and configured to detect acceleration of the wearable ECG system and output an electrical signal accordingly. The processor is configured to receive the electrical signal from the motion detection module, and control the multiplexor to selectively transmit output of the electrodes to the analog detection module or the digital detection module based on the electrical signal.

The electrical signal may be a voltage value that indicates the acceleration of the wearable ECG system. The processor may be configured to compare the voltage value to a predetermined value; if the voltage value is less than the predetermined value, the processor may be configured to control the multiplexor to transmit the output of the electrodes to the analog detection module; if the voltage value is equal to or greater than the predetermined value, the processor may be configured to control the multiplexor to transmit the output of the electrodes to the digital detection module.

The analog detection module may include: a first amplifier configured to receive and amplify ECG signals from a plurality of electrodes; a second amplifier connected with the first amplifier, and configured to amplify output of the first amplifier in a first bandwidth; a third amplifier connected with the first amplifier, and configured to amplify output of the first amplifier in a second bandwidth; a voltage adder connected with the third amplifier, and configured to output sum of output voltage of the third amplifier and a calibration voltage; a comparator connected with the second amplifier and the voltage adder, and configured to compare output of the second amplifier and output of the voltage adder, and output a signal accordingly; and a calibration voltage generator connected with output of the comparator, and configured to generate the calibration voltage according to the output of the comparator. The calibration voltage generator may be configured to vary the calibration voltage until the output of the comparator meets a predetermined requirement.

The first bandwidth of the second amplifier may include a frequency range of QRS complex of an ECG signal, while the second bandwidth of the third amplifier may be in a lower frequency range than the first bandwidth. The second bandwidth may only include frequencies of baseline drifts.

The calibration voltage generator may be configured to sweep the calibration voltage from zero to a predetermined maximum value until the output of the comparator meets a requirement of being a pulse with periods in the range of human heart beat intervals, the variation of the periods being smaller than a predetermined threshold.

The calibration voltage generator may be configured to sweep the calibration voltage until the output of the comparator meets the requirement for a predetermined number of cycles. The wearable ECG system may further include an alarming module. After the predetermined number of cycles of sweeping the calibration voltage, if the output of the comparator fails to meet the requirement, the alarming module may be configured to transmit an alert to the user.

The digital detection module may include a fourth amplifier; a fifth amplifier being connected with the fourth amplifier; an ADC being connected with the fifth amplifier; and a digital signal processing circuit being connected with the ADC. The digital signal processing circuit and the ADC may be respectively connected with the processor.

The fourth amplifier may have a gain of 30 dB-36 dB, while the fifth amplifier may have a gain of 18 dB-25 dB. The digital signal processing circuit may include a first filter; a second filter; a third filter, the second and the third filters being respectively connected with the first filter; a waveform buffer being connected with the first, second and third filters respectively; and a maximum value searcher being connected with the second and the third filters and the processor respectively.

The first filter may be a QSWT (Quadratic Spline Wavelet) filter configured to filter baseline shift of the wearable ECG system and human caused noise. The second and the third filters may be respectively configured to execute STAC (Short-term Autocorrelation) algorithm so as to filter myoelectric noise and noise caused by motion of the electrodes. The QSWT filter may include multiple adders and multiple shift operators, while the second and the third filters may respectively include a correlation coefficient buffer, the correlation coefficient buffers of the second and the third filters being respectively synchronized with the ADC.

The second and the third filters may be configured to execute computation in an alternating fashion, the computing time of which are overlapped by a predetermined period.

In yet another aspect, the present patent application provides a wearable ECG system that includes: a plurality of electrodes; a multiplexor, the multiplexor including an input port, two output ports, and a control port, the input port of the multiplexor being connected with the electrodes; an analog detection module being connected with one output port of the multiplexor; a digital detection module being connected with the other output port of the multiplexor; a processor being connected with the control port of the multiplexor and the digital detection module; and a motion detection module, connected with the processor and configured to detect acceleration of the wearable ECG system and output an electrical signal accordingly. The processor is configured to receive the electrical signal from the motion detection module, and control the multiplexor to selectively transmit output of the electrodes to the analog detection module or the digital detection module based on the electrical signal. The analog detection module includes: a first amplifier configured to receive and amplify ECG signals from a plurality of electrodes; a second amplifier connected with the first amplifier, and configured to amplify output of the first amplifier in a first bandwidth; a third amplifier connected with the first amplifier, and configured to amplify output of the first amplifier in a second bandwidth; a voltage adder connected with the third amplifier, and configured to output sum of output voltage of the third amplifier and a calibration voltage; a comparator connected with the second amplifier and the voltage adder, and configured to compare output of the second amplifier and output of the voltage adder, and output a signal accordingly; and a calibration voltage generator connected with output of the comparator, and configured to generate the calibration voltage according to the output of the comparator. The calibration voltage generator is configured to vary the calibration voltage until the output of the comparator meets a predetermined requirement. The digital detection module includes: a fourth amplifier; a fifth amplifier being connected with the fourth amplifier; an ADC being connected with the fifth amplifier; and a digital signal processing circuit being connected with the ADC. The digital signal processing circuit and the ADC are respectively connected with the processor.

The fourth amplifier may have a gain of 30 dB-36 dB, while the fifth amplifier may have a gain of 18 dB-25 dB. The digital signal processing circuit may include a first filter; a second filter; a third filter, the second and the third filters being respectively connected with the first filter; a waveform buffer being connected with the first, second and third filters respectively; and a maximum value searcher being connected with the second and the third filters and the processor respectively. The second and the third filters may be configured to execute computation in an alternating fashion, the computing time of which are overlapped by a predetermined period.

DETAILED DESCRIPTION

Reference will now be made in detail to a preferred embodiment of the wearable ECG system disclosed in the present patent application, examples of which are also provided in the following description. Exemplary embodiments of the wearable ECG system disclosed in the present patent application are described in detail, although it will be apparent to those skilled in the relevant art that some features that are not particularly important to an understanding of the wearable ECG system may not be shown for the sake of clarity.

Furthermore, it should be understood that the wearable ECG system disclosed in the present patent application is not limited to the precise embodiments described below and that various changes and modifications thereof may be effected by one skilled in the art without departing from the spirit or scope of the protection. For example, elements and/or features of different illustrative embodiments may be combined with each other and/or substituted for each other within the scope of this disclosure.

Figure 1:
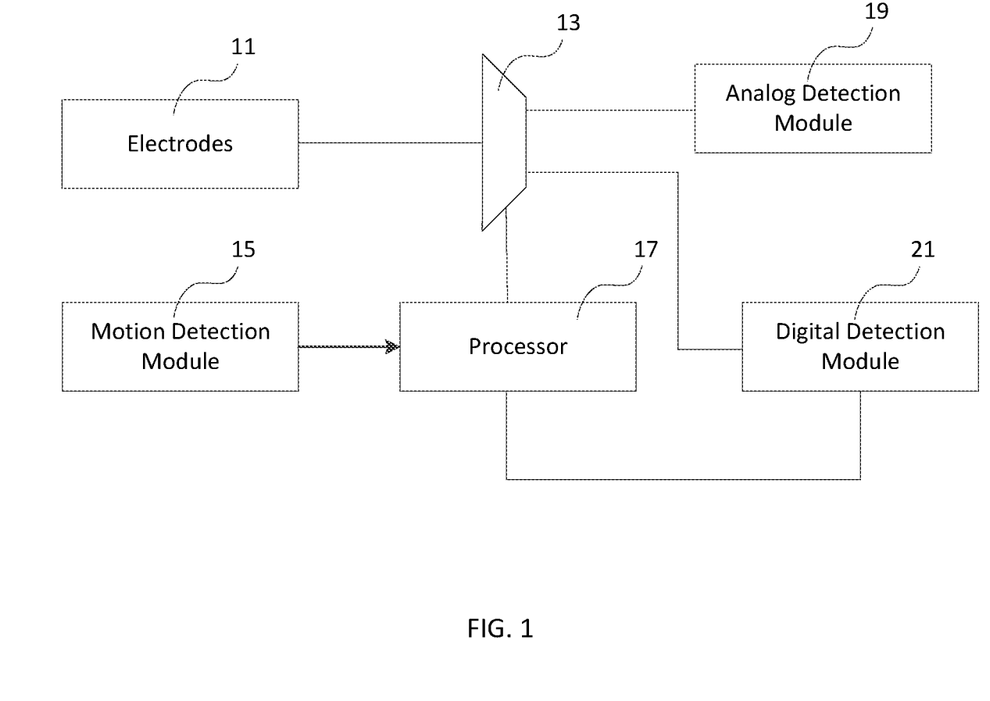
FIG. 1 is a block diagram of a wearable ECG system in accordance with an embodiment of the present patent application.

FIG. 1 is a block diagram of a wearable ECG system in accordance with an embodiment of the present patent application. Referring to FIG. 1, the wearable ECG system includes a number of electrodes 11; a multiplexor 13 that includes an input port, two output ports, and a control port, the input port of the multiplexor 13 being connected with the electrodes 11; an analog detection module 19 being connected with one output port of the multiplexor 13; a digital detection module 21 being connected with the other output port of the multiplexor 13; a processor 17 connected with the control port of the multiplexor 13 and the digital detection module 21; and a motion detection module 15, connected with the processor 17 and configured to detect acceleration of the wearable ECG system and output an electrical signal accordingly. The processor 17 is configured to receive the electrical signal from the motion detection module 15, and control the multiplexor 13 to selectively transmit output of the electrodes 11 to the analog detection module 19 or the digital detection module 21 based on the electrical signal.

More specifically, the electrical signal is a voltage value that indicates the acceleration of the wearable ECG system. The processor 17 is configured to compare the voltage value to a predetermined value. If the voltage value is less than the predetermined value, it means the acceleration of the wearable ECG system is relatively low, and the processor 17 is configured to control the multiplexor 13 to transmit the output of the electrodes 11 to the analog detection module 19, so that the analog detection module 19 is configured to execute the detection of ECG signals. If the voltage value is equal to or greater than the predetermined value, it means the acceleration of the wearable ECG system is relatively high, and the processor 17 is configured to control the multiplexor 13 to transmit the output of the electrodes 11 to the digital detection module 21, so that the digital detection module 21 is configured to execute the detection of ECG signals.

Figure 2:
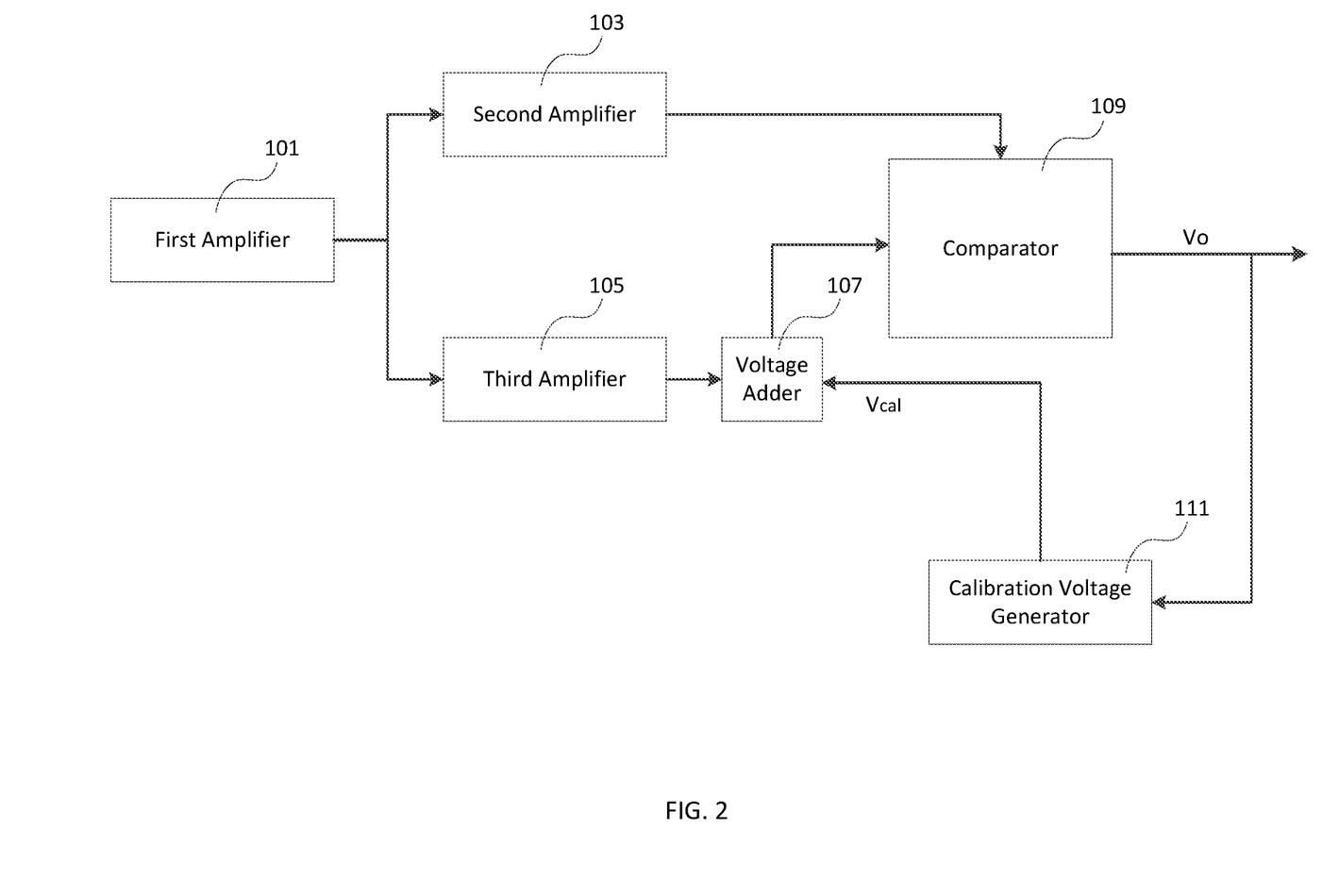
FIG. 2 is a block diagram of an analog detection module in the wearable ECG system depicted in FIG. 1.

FIG. 2 is a block diagram of the analog detection module 19 in the wearable ECG system depicted in FIG. 1. Referring to FIG. 2, the analog detection module 19 includes a first amplifier 101 configured to receive and amplify ECG signals from a plurality of electrodes; a second amplifier 103 connected with the first amplifier 101, and configured to amplify output of the first amplifier 101 in a first bandwidth; a third amplifier 105 connected with the first amplifier 101, and configured to amplify output of the first amplifier 101 in a second bandwidth; a voltage adder 107 connected with the third amplifier 105, and configured to output sum of output voltage of the third amplifier 105 and a calibration voltage $V_{cal}$; a comparator 109 connected with the second amplifier 103 and the voltage adder 107, and configured to compare output of the second amplifier 103 and output of the voltage adder 107, and output a signal $V_o$ accordingly; and a calibration voltage generator 111 connected with output of the comparator 109, and configured to generate the calibration voltage $V_{cal}$ according to the output of the comparator 109.

The first bandwidth of the second amplifier 103 includes the frequency range of QRS complex of an ECG signal, while the second bandwidth of the third amplifier 105 is in a lower frequency range than the first bandwidth, including only frequencies of baseline drifts, which may be caused by motion of the user being examined, or by change of the operating environment of the system. The gain of the second amplifier 103 is equal to the gain of the third amplifier 105.

In this embodiment, the first amplifier 101 is a programmable gain amplifier. Preferably, the programmable gain amplifier is a low noise amplifier. The second amplifier 103 and the third amplifier 105 each include a two stage Miller-compensated operational amplifier. The voltage adder 107 is implemented by a switched capacitor network. The comparator 109 is a dynamic latched comparator, which consumes power only when latching.

In operation, the first amplifier 101 receives ECG signals from a number of electrodes, amplifies the signals and sends the amplified signals to the second amplifier 103 and the third amplifier 105. Because of the above configuration of the bandwidths of the second amplifier 103 and the third amplifier 105, the output of the second amplifier 103 contains the QRS complex voltage $V_Q$, while the output of the third amplifier 105 contains the baseline drifts voltage $V_B$. The voltage adder 107 adds the output of the third amplifier 105 and the calibration voltage $V_{cal}$, and output $(V_B+V_{cal})$ to the comparator 109.

Figure 3:
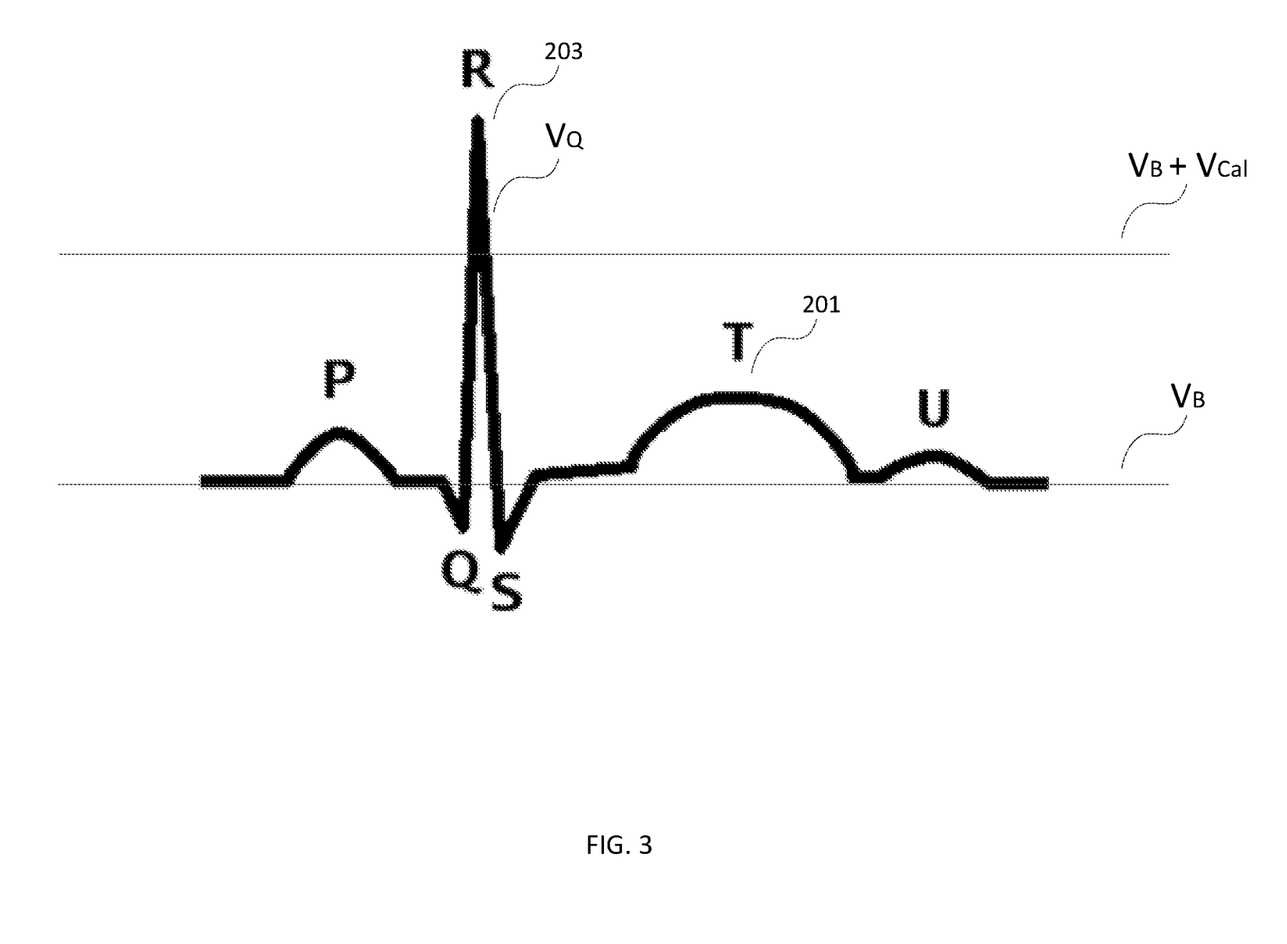
FIG. 3 illustrate different voltage levels with respect to an ECG signal.

FIG. 3 illustrate different voltage levels with respect to an ECG signal. Referring to FIGS. 2 and 3, the comparator 109 is configured to compare the QRS complex voltage $V_Q$ and $(V_B+V_{cal})$. If $V_Q>(V_B+V_{cal})$, the comparator 109 is configured to output a high voltage that corresponds to digital "1"; otherwise, the comparator 109 is configured to output a low voltage that corresponds to digital "0". If $V_{cal}$ is chosen appropriately, when the comparator 109 outputs a digital "1", a heartbeat is detected. It can be seen that in order for the system to detect heart beats correctly, $V_{cal}$ should be chosen so that $(V_B+V_{cal})$ is above the peak of T-wave 201, but below the peak of R-wave 203.

In this embodiment, the calibration voltage generator 111 is configured to vary the calibration voltage $V_{cal}$ until the output of the comparator 109 meets a predetermined set of requirements. More specifically, the calibration voltage generator 111 is configured to sweep the calibration voltage $V_{cal}$ from zero to a predetermined maximum value until the output voltage of the comparator 109 $V_o$ becomes a pulse with periods in the range of human heart beat intervals, and the variation of the periods is smaller than a predetermined threshold. The above calibration process may be repeated by a predetermined number of cycles at the beginning of an examination of a user. The calibration voltage generator 111, which may be controlled by a microcontroller, which is powered off after the calibration cycles are completed.

During examination of the user, the microcontroller may be configured to control the calibration voltage generator 111 to vary and calibrate the calibration voltage $V_{cal}$ again, if the output of the comparator 109 $V_o$ doesn't meet the above predetermined set of requirements. Such situation may be caused by, for example, that the user being examined moves the system accidentally with respect to his/her body, or there are changes on the system's operating environment. More specifically, if $V_o$ is no longer a pulse with periods in the range of human heart beat intervals, or if the variation of the periods is smaller than the predetermined threshold, the calibration voltage generator 111 is configured to vary and calibrate the calibration voltage $V_{cal}$ again.

At the beginning of the examination or in the middle of the examination, if the output of the comparator 109 $V_o$ not meeting the above predetermined requirements is caused by irregular R-waves of the user, the calibration process will fail to complete. After a predetermined number of cycles of sweeping the calibration voltage $V_{cal}$, if the requirements are still not met, the system is configured to transmit an alert to the user, indicating detection of possible heart problems such as arrhythmia of the user. In this embodiment, the predetermined number of cycles of sweeping the calibration voltage $V_{cal}$ is 10. It is noted that, in an embodiment, the system further includes an alarming module (not shown in FIG. 1). The alarming module is configured to transmit the alert to the user.

In the process of the analog detection module 19 detecting the ECG, both ADC and digital signal processor are not required to accurately determine the timing of R-wave peaks. Both power consumption and circuit complexity of the system are greatly reduced. The whole wearable ECG system can be integrated onto an ASIC chip. Therefore the wearable ECG system is particularly suitable to be worn by a user and used to monitor the user's heart condition in real time. However, when the person being examined is in motion, the acceleration of the wearable ECG system may reach or be higher than the predetermined value. If the analog detection module 19 is continued to be used to acquire the ECG data, relatively large errors may present in the test results. Therefore, when this condition is detected, the processor 17 is configured to control the multiplexor 13 to transmit electrical signals from the electrodes 11 to the digital detection module 21, which is configured to execute more accurate detection.

Figure 4:
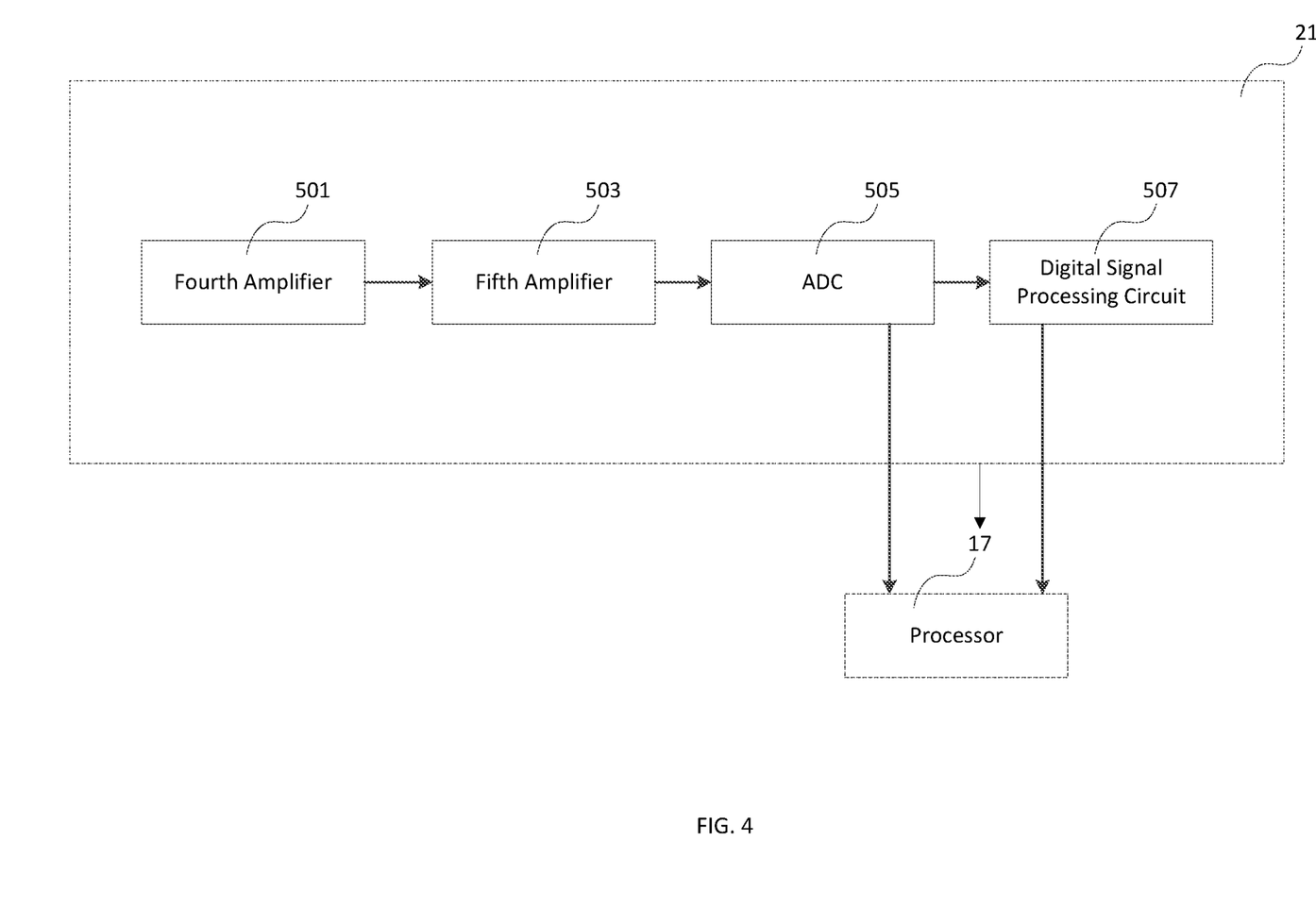
FIG. 4 is a block diagram of a digital detection module in the wearable ECG system depicted in FIG. 1.

FIG. 4 is a block diagram of the digital detection module 21 in the wearable ECG system depicted in FIG. 1. Referring to FIG. 4, the digital detection module 21 includes a fourth amplifier 501; a fifth amplifier 503 being connected with the fourth amplifier 501; an ADC 505 being connected with the fifth amplifier 503; and a digital signal processing circuit 507 being connected with the ADC 505. The digital signal processing circuit 507 and the ADC 505 are respectively connected with the processor 17. In this embodiment, preferably, the fourth amplifier 501 has a gain of 30 dB-36 dB. The fifth amplifier has a gain of 18 dB-25 dB.

Figure 5:
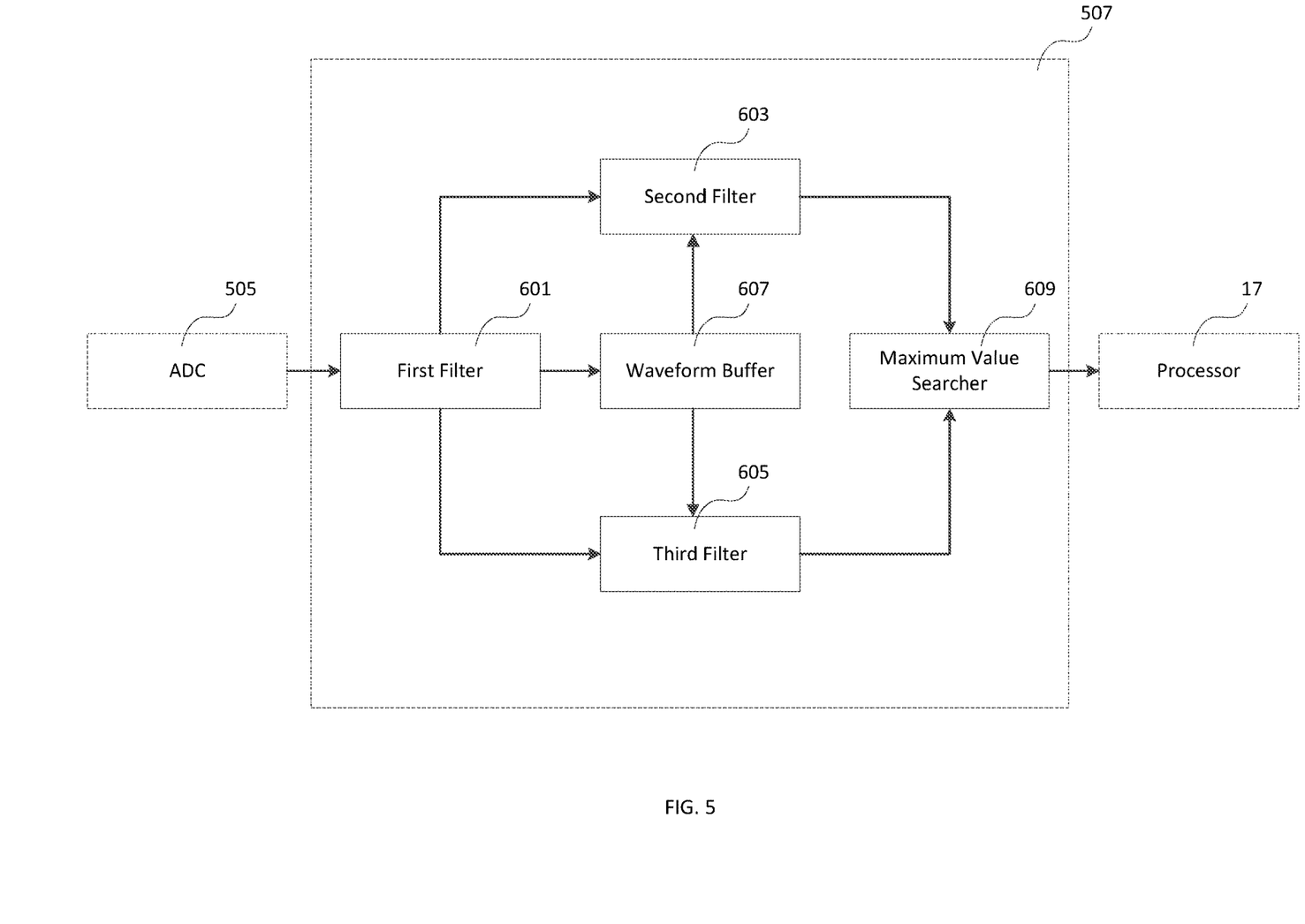
FIG. 5 is a block diagram of a digital signal processing circuit in the digital detection module depicted in FIG. 4.

FIG. 5 is a block diagram of the digital signal processing circuit 507 in the digital detection module 21 depicted in FIG. 4. Referring to FIG. 5, the digital signal processing circuit 507 includes a first filter 601; a second filter 603; a third filter 605, the second and the third filters 603 and 605 are respectively connected with the first filter 601; a waveform buffer 607 being connected with the first, second and third filters 601, 603 and 605 respectively; and a maximum value searcher 609 being connected with the second and the third filters 603 and 605, and the processor 17 respectively.

In this embodiment, the first filter 601 is a QSWT (Quadratic Spline Wavelet) filter being configured to filter baseline shift of the system and human caused noise. The QSWT filter 601 includes multiple adders and multiple shift operators. The amount of computing executed by the QSWT filter 601 is relatively small, and thus the power consumption of the QSWT filer 601 is relatively low.

The second and the third filters 603 and 605 are respectively configured to execute STAC (Short-term Autocorrelation) algorithm so as to filter myoelectric noise and noise caused by motion of the electrodes. The second and the third filters 603 and 605 respectively include a correlation coefficient buffer. The correlation coefficient buffers of the second and the third filters 603 and 605 are respectively synchronized with the ADC 505. In this embodiment, the second and the third filters 603 and 605 are configured to execute computation in an alternating fashion, the computing time of which are overlapped by a predetermined period. Preferably, the updating period of the maximum value searcher 609 is 1 second, while the predetermined period is 0.5 second. The above-mentioned configuration decreases the operational frequency to execute STAC computation, which can even be made lower than the clock frequency, so that power consumption of the system is further lowered.

In the wearable ECG system provided by the above embodiments, when the motion detection module 15 detects that the current acceleration of the system is relatively low, the processor 17 controls the analog detection module 19 to execute the detection of ECG signals. The complexity and the power consumption of the analog detection module 19 are both relatively low, which keeps the power consumption of the whole system at a relatively low level for many application scenarios. When the motion detection module 15 detects that the current acceleration of the system is relatively high, the processor 17 controls the digital detection module 21 to execute the detection of ECG signals. The digital detection module 21 deploys QSWT filters and STAC algorithm and is capable of effectively filter out baseline shifting, human noise, myoelectric noise and noise cause by the motion of the electrodes. At the same time, the second and the third filters 603 and 605 compute in an alternating fashion, the computing time of which have an overlap of a time period of predetermined length, which decreases the operating frequency for STAC computation to be even lower than the clock frequency of the system, so as to further reduce the power consumption of the system. As a result, the wearable ECG system provided by the above embodiment can ensure accurate detection of ECG data while keeping the overall power consumption relatively low, so as to meet requirements of wearable applications.

While the present patent application has been shown and described with particular references to a number of embodiments thereof, it should be noted that various other changes or modifications may be made without departing from the scope of the present invention.

What is claimed is:

1. A wearable ECG system comprising:
a plurality of electrodes;
a multiplexor, the multiplexor comprising an input port, two output ports, and a control port, the input port of the multiplexor being connected with the electrodes and configured to selectively direct signals from all of the electrodes to one of the two output ports based on an electrical signal from the control port;
an analog detection module being connected with one output port of the multiplexor;
a digital detection module being connected with the other output port of the multiplexor;
a processor being connected with the control port of the multiplexor and the digital detection module; and
a motion detection module, connected with the processor and configured to detect acceleration of the wearable ECG system and output an electrical signal accordingly; wherein:
the processor is configured to receive the electrical signal from the motion detection module, and control the multiplexor through the control port to selectively transmit output of all of the electrodes to the analog detection module or the digital detection module based on the electrical signal; and the analog detection module is configured to detect a heart beat solely without utilizing any portion of the digital detection module.

2. The wearable ECG system of claim 1, wherein the electrical signal is a voltage value that indicates the acceleration of the wearable ECG system; the processor is configured to compare the voltage value to a predetermined value; if the voltage value is less than the predetermined value, the processor is configured to control the multiplexor to transmit the output of the electrodes to the analog detection module; if the voltage value is equal to or greater than the predetermined value, the processor is configured to control the multiplexor to transmit the output of the electrodes to the digital detection module.

3. The wearable ECG system of claim 1, wherein the analog detection module comprises:
 a first amplifier configured to receive and amplify ECG signals from a plurality of electrodes;
 a second amplifier connected with the first amplifier, and configured to amplify output of the first amplifier in a first bandwidth;
 a third amplifier connected with the first amplifier, and configured to amplify output of the first amplifier in a second bandwidth;
 a voltage adder connected with the third amplifier, and configured to output a sum of an output voltage of the third amplifier and a calibration voltage;
 a comparator connected with the second amplifier and the voltage adder, and configured to compare output of the second amplifier and output of the voltage adder, and output a signal accordingly; and
 a calibration voltage generator connected with output of the comparator, and configured to generate the calibration voltage according to the output of the comparator; the calibration voltage generator is configured to vary the calibration voltage until the output of the comparator meets a predetermined requirement.

4. The wearable ECG system of claim 3, wherein the first bandwidth of the second amplifier comprises a frequency range of QRS complex of an ECG signal, while the second bandwidth of the third amplifier is in a lower frequency range than the first bandwidth, the second bandwidth comprising only frequencies of baseline drifts.

5. The wearable ECG system of claim 3, wherein the calibration voltage generator is configured to sweep the calibration voltage from zero to a predetermined maximum value until the output of the comparator meets a requirement of being a pulse with periods in the range of human heart beat intervals, the variation of the periods being smaller than a predetermined threshold.

6. The wearable ECG system of claim 5, wherein the calibration voltage generator is configured to sweep the calibration voltage until the output of the comparator meets the requirement for a predetermined number of cycles.

7. The wearable ECG system of claim 5 further comprising an alarming module, wherein after the predetermined number of cycles of sweeping the calibration voltage, if the output of the comparator fails to meet the requirement, the alarming module is configured to transmit an alert to the user.

8. The wearable ECG system of claim 1, wherein the digital detection module comprises a first amplifier; a second amplifier being connected with the first amplifier; an ADC being connected with the second amplifier; and a digital signal processing circuit being connected with the ADC; the digital signal processing circuit and the ADC are respectively connected with the processor.

9. The wearable ECG system of claim 8, wherein the fourth amplifier has a gain of 30 dB-36 dB, while the fifth amplifier has a gain of 18 dB-25 dB.

10. The wearable ECG system of claim 8, wherein the digital signal processing circuit comprises a first filter; a second filter; a third filter, the second and the third filters being respectively connected with the first filter; a waveform buffer being connected with the first, second and third filters respectively; and a maximum value searcher being connected with the second and the third filters and the processor respectively.

11. The wearable ECG system of claim 10, wherein the first filter is a QSWT (Quadratic Spline Wavelet) filter configured to filter baseline shift of the wearable ECG system and human caused noise; the second and the third filters are respectively configured to execute STAC (Short-term Autocorrelation) algorithm so as to filter myoelectric noise and noise caused by motion of the electrodes.

12. The wearable ECG system of claim 11, wherein the QSWT filter comprises multiple adders and multiple shift operators, while the second and the third filters respectively comprise a correlation coefficient buffer, the correlation coefficient buffers of the second and the third filters being respectively synchronized with the ADC.

13. The wearable ECG system of claim 10, wherein the second and the third filters are configured to execute computation in an alternating fashion, the computing time of which are overlapped by a predetermined period.

14. A wearable ECG system comprising:
 a plurality of electrodes;
 a multiplexor, the multiplexor comprising an input port, two output ports, and a control port, the input port of the multiplexor being connected with the electrodes;
 an analog detection module being connected with one output port of the multiplexor;
 a digital detection module being connected with the other output port of the multiplexor;
 a processor being connected with the control port of the multiplexor and the digital detection module; and
 a motion detection module, connected with the processor and configured to detect acceleration of the wearable ECG system and output an electrical signal accordingly; wherein:
 the processor is configured to receive the electrical signal from the motion detection module, and control the multiplexor through the control port to selectively transmit output of all of the electrodes to the analog detection module or the digital detection module based on the electrical signal; and
 the analog detection module is configured to detect a heart beat solely without utilizing any portion of the digital detection module.

15. The wearable ECG system of claim 14, wherein the processor is configured to compare the voltage value to a predetermined value; if the voltage value is less than the predetermined value, the processor is configured to control the multiplexor to transmit the output of the electrodes to the analog detection module; if the voltage value is equal to or greater than the predetermined value, the processor is configured to control the multiplexor to transmit the output of the electrodes to the digital detection module.

16. The wearable ECG system of claim 14, wherein the analog detection module comprises:
 a first amplifier configured to receive and amplify ECG signals from a plurality of electrodes;

a second amplifier connected with the first amplifier, and configured to amplify output of the first amplifier in a first bandwidth;

a third amplifier connected with the first amplifier, and configured to amplify output of the first amplifier in a second bandwidth;

a voltage adder connected with the third amplifier, and configured to output a sum of an output voltage of the third amplifier and a calibration voltage;

a comparator connected with the second amplifier and the voltage adder, and configured to compare output of the second amplifier and output of the voltage adder, and output a signal accordingly; and a calibration voltage generator connected with output of the comparator, and configured to generate the calibration voltage according to the output of the comparator; the calibration voltage generator is configured to vary the calibration voltage until the output of the comparator meets a predetermined requirement.

17. The wearable ECG system of claim 16, wherein the calibration voltage generator is configured to sweep the calibration voltage from zero to a predetermined maximum value until the output of the comparator meets a requirement of being a pulse with periods in the range of human heart beat intervals, the variation of the periods being smaller than a predetermined threshold.

18. A wearable ECG system comprising:
a multiplexor, the multiplexor comprising an input port, two output ports, and a control port, the input port of the multiplexor being connected with a plurality of electrodes and configured to selectively direct signals from all of the electrodes to one of the two output ports based on an electrical signal from the control port;

an analog detection module being connected with one output port of the multiplexor;

a digital detection module being connected with the other output port of the multiplexor; and a processor being connected with the control port of the multiplexor and the digital detection module and configured to receive the electrical signal and control the multiplexor through the control port to selectively transmit output of all of the electrodes to the analog detection module or the digital detection module based on the electrical signal; wherein:

the analog detection module is configured to detect a heart beat solely without utilizing any portion of the digital detection module.

19. The wearable ECG system of claim 18 further comprising a motion detection module, wherein the motion detection module is connected with the processor and configured to detect acceleration of the wearable ECG system and output the electrical signal accordingly.

20. The wearable ECG system of claim 19, wherein the analog detection module comprises:
a first amplifier configured to receive and amplify ECG signals from a plurality of electrodes;

a second amplifier connected with the first amplifier, and configured to amplify output of the first amplifier in a first bandwidth;

a third amplifier connected with the first amplifier, and configured to amplify output of the first amplifier in a second bandwidth;

a voltage adder connected with the third amplifier, and configured to output a sum of an output voltage of the third amplifier and a calibration voltage;

a comparator connected with the second amplifier and the voltage adder, and configured to compare output of the second amplifier and output of the voltage adder, and output a signal accordingly; and a calibration voltage generator connected with output of the comparator, and configured to generate the calibration voltage according to the output of the comparator; the calibration voltage generator is configured to vary the calibration voltage until the output of the comparator meets a predetermined requirement.

* * * * *